United States Patent [19]

Ruckelshauss

[11] 4,048,243
[45] Sept. 13, 1977

[54] METHOD FOR THE PRODUCTION OF ETHYLBENZENE

[75] Inventor: Gerhard Ruckelshauss, Dorsten, Germany

[73] Assignee: Chemische Werke Huls Aktiengesellschaft, Marl, Germany

[21] Appl. No.: 646,944

[22] Filed: Jan. 6, 1976

[30] Foreign Application Priority Data

Mar. 18, 1975   Germany ............................. 2511674

[51] Int. Cl.$^2$ ............................................. C07C 15/02
[52] U.S. Cl. ........................... 260/668 D; 260/666 A
[58] Field of Search ........ 260/666 A, 666 PY, 668 D, 260/666 B

[56] References Cited

U.S. PATENT DOCUMENTS

| | | | |
|---|---|---|---|
| 2,745,887 | 5/1956 | Pines et al. | 260/666 A |
| 2,836,633 | 5/1958 | Esmay et al. | 260/671 R |
| 3,897,508 | 7/1975 | Tkatchenko | 260/666 B |
| 3,903,185 | 9/1975 | Vogel et al. | 260/668 D |
| 3,917,730 | 11/1975 | Tkatchenko | 260/666 PY |

*Primary Examiner*—Veronica O'Keefe
*Attorney, Agent, or Firm*—Gilbert L. Wells

[57] ABSTRACT

Method for the production of ethylbenzene by the dehydrogenation of cycloolefins containing 8 carbon atoms and two double bonds in the presence of aromatization catalysts. The cycloolefin ring contains 6 carbon atoms and at least one double bond. These cycloolefins are treated at temperatures of about 20° – 150° C and under pressures of about 0.8 – 2 atmospheres with an aromatization catalyst containing 5 – 25 percent by weight of an alkali metal and 75 – 95 percent by weight of aluminum oxide as the support.

10 Claims, No Drawings

4,048,243

METHOD FOR THE PRODUCTION OF ETHYLBENZENE

CROSS REFERENCE TO A RELATED APPLICATION

Applicant claims priority under 35 U.S.C. 119 for Application P 25 11 674.9, filed Mar. 18, 1975 in the Patent Office of the Federal Republic of Germany.

BACKGROUND OF THE INVENTION

The field of the invention is dehydrogenation of aromatic carbon compounds and the present invention is particularly related to a method for the production of ethylbenzene by the dehydrogenation of cycloolefins having 8 carbon atoms in the presence of an aromatization catalyst.

Ethylbenzene is produced on a commercial scale by the alkylation of benzene with ethylene. Inasmuch as a constantly growing demand for aromatics is to be expected, one can also reckon with an increasing shortage of benzene.

The state of the art of ethylbenzene manufacture may be ascertained by reference to Kirk-Othmer "Encyclopedia of Chemical Technology", Vol. 19, 2nd Edition (1969), pp 57–62 and U.S. Pat. No. 3,903,185 the disclosures of which are incorporated herein. The state of the art of dehydrogenating non-aromatic cyclic compounds to aromatic compounds may be ascertained by reference to U.S. Pat. No. 2,745,887. The raw materials of the present invention are prepared as disclosed in U.S. Pat. Nos. 3,897,508 and 3,917,730, and the catalysts are prepared as disclosed in U.S. Pat. No. 2,836,633 and British Patent 1,259,535, the disclosures of which are incorporated herein.

Attempts have already been made to produce ethylbenzene by methods other than alkylation of benzene with ethylene.

U.S. Pat. No. 2,745,887 discloses a process for treating with alkali metals cyclic hydrocarbons having 6 carbon atoms in the ring and containing at least two double bonds, at least one of them in the ring. However, this process is useless for commercial purposes since induction periods of 12–15 hours occur before the reaction is initiated, unless activators are added such as, for example, o-chlorotoluene, which reduce the induction period to 4 - 5 hours, or unless the process is carried out in the presence of extremely expensive and dangerous sodium hydride. However, even in these cases, only degrees of conversion of up to 71 percent are attained. Furthermore, it was found that this process does not yield useful results when vinylcyclohexene is used.

Furthermore, it is known from U.S. Pat. No. 3,903,185 that cycloolefins having 8 carbon atoms can be conducted over catalysts of Subgroups VI to VIII, including the platinum group, of the Periodic Table of the elements, at temperatures of 350°–450° C, under pressures of 2.5 - 30 atmospheres absolute and in the presence of 0.2 - 20 m³ of hydrogen per kilogram of $C_8$-cycloolefin, to obtain ethylbenzene in rather satisfactory yields. However, this process is commercially very expensive, because it must be carried out at high temperatures, under pressure, and in the presence of hydrogen.

SUMMARY OF THE INVENTION

Having in mind the limitations of the prior art, it is an object of the present invention to provide a process for the production of ethylbenzene from cycloolefins of 8 carbon atoms which can be conducted in a simple way, rapidly, at low temperature, and without excess pressure.

This object is achieved by a process for the dehydrogenation to aromatic compounds of cycloolefins containing 8 carbon atoms and 2 double bonds, with 6 carbon atoms and at least 1 double bond in the ring. The improvement of the present invention requres that the cycloolefins be treated at temperatures of about 20° – 150° C and under pressures of about 0.8 – 2 atmospheres with a catalyst containing about 5 – 25 percent by weight of an alkali metal (based on the finished catalyst) on 75 – 95 percent by weight aluminum oxide as the support.

DESCRIPTION OF THE PREFERRED EMBODIMENTS

Suitable starting materials for the process of the present invention are cycloolefins containing 8 carbon atoms as well as 2 double bonds, with the further limitation that 6 carbon atoms and at least one double bond are present in the ring. Examples of the cycloolefins useful in the present invention include, but are not limited to: isomeric ethylidenecyclohexenes especially cis- and trans-(1)-ethylidene-cyclohexene-(2), the isomeric ethylcyclohexadienes especially 1-ethyl-cyclohexadiene-(1,3), 2-ethyl-cyclo-hexadiene-(1,3) and 1-ethyl-cyclohexadiene-(1,4), the isomeric vinylcyclohexenes, especially 1-vinylcyclohexene-3.

The aforementioned cycloolefins are readily accessible commercially, for example by the dimerization of butadiene or by the use of $C_4$-fractions, as disclosed in U.S. Pat. Nos. 3,897,508 and 3,917,730; furthermore, they are obtained as by-products during the commercial production of 1,5,9-cyclododecatriene.

Surprisingly, a spontaneous evolution of hydrogen occurs during the process of the present invention at room temperature (20° C) without observing any appreciable induction period. At temperatures below 20° C, the reaction proceeds very slowly.

When the temperature is raised to above 150° C, the formation of undesired by-products is found to an increasing extent, such as, for example, ethylcyclohexane produced by a hydrogenation reaction. An especially advantageous temperature range is between about 40° and 130° C, because in this temperature zone the reaction takes place with sufficient speed and without interfering side reactions.

The reaction should take place within a pressure range of about 0.8 – 2 atmospheres. At below 0.8 atmosphere, higher requirements must be met by the apparatus. If the limit of 2 atmospheres is exceeded, disadvantageous hydrogenation reactions are also observed. Especially preferred is the use of normal pressure, since this mode of operation yields good results and can be realized commercially in an especially simple way. Thus, this procedure readily avoids, for example, the danger of the penetration of air into the apparatus, which occurs when operating with subatmospheric pressure, and furthermore sealing problems are avoided which occur when operating under excess pressure.

An alkali metal is used as the catalyst on aluminum oxide as the support. For production of the support, a great variety of the modifications of aluminum oxide are suitable, such as the α-, κ-, H-, δ-, γ-, η-, H-, or δ-modifications; however, γ-aluminum oxide is generally preferred since it is easiest in its manipulation and yields satisfactory results.

To ensure a good efficiency of the catalyst, the specific surface area of the support material should generally be larger than 25 m²/g, preferably larger than 100 m²/g.

Suitable alkali metals are lithium, sodium, potassium, rubidium, cesium, or mixtures of the aforementioned alkali metals. Also, alloys containing two or more alkali metals may be used. A typical example of such an alloy is a potassium-sodium alloy. Preferably, sodium is used as the alkali metal, since it is relatively harmless and tends less toward side reactions.

The catalyst contains about 2 – 25 percent by weight of the alkali metal (based on the finished catalyst). At concentrations below 5 percent by weight, an isomerization takes place to a predominant extent and at concentrations above 25 percent by weight, the catalyst is more difficult to handle, since it is less pourable.

Preferably, however, the catalyst contains about 8 – 15 percent by weight of alkali metal, since high activity connected with an excellent pourability is found in this range. Excellent results are obtained with a catalyst containing about 10 percent by weight of alkali metal.

The amount of catalyst suitably employed for the reaction should be large enough that the weight ratio of alkali metal to cycloolefin is 1 : 1000 to 1 : 30. Below a ratio of 1 : 1000, the reaction time is too long. Above the ratio of 1 : 30, the evolution of hydrogen becomes too vigorous. A ratio of 1 : 150 to 1 : 50 is particularly advantageous. Within this ratio, the reaction can be controlled without danger.

The manufacturing methods for catalysts containing alkali metals on an aluminum oxide support have been well known to those skilled in the art for years and are disclosed in detail in numerous popular publications such as, for example, Houben Weyl, "Methoden der organischen Chemie" [Methods of Organic Chemistry] 14/1: 635 (1961), and also in numerous patents, such as, for example, U.S. Pat. No. 2,836,633 and British Pat. No. 1,259,535.

In a preferred embodiment, the catalyst is produced in accordance with a very simple method by first pre-drying the support material for about 5 – °hours at a temperature of about 200° – 400° C. After drying, the support material is allowed to cool to about 150° C and then the corresponding amount of alkali metal is added in a mechanical mixing device (under a protective gas atmosphere). At the temperature employed, the metal melts and is, due to the mixing step, uniformly distributed on the support material. If desired, the catalyst can furthermore be subjected conventionally to a high temperature aftertreatment, for example by heating the same for about 2 – 20 hours to about 200° – 400° C.

After its manufacture, the catalyst is present in the form of a powder or granules. However, it is also possible to coat supports present in formed pieces with the alkali metal and in such cases, catalysts consisting of individual pieces are obtained.

The process of the present invention can be conducted continuously or discontinuously. In this connection, various modifications of the process can be used. Thus, it is possible, for example, to bring the cycloolefin to the desired reaction temperature, and the catalyst can be added gradually in small amounts continuously or discontinuously in accordance with the liberation of hydrogen. A further possibility resides in providing the catalyst in ethylbenzene and adding the cycloolefin at the desired reaction temperature at such a rate that the evolution of hydrogen can still be kept under control. The progress of the reaction can be controlled by measuring the index of refraction and/or by gas chromatography. When the reaction loses its vigor, the addition of further catalyst is advantageous in certain cases.

The reaction is ordinarily conducted in a protective gas atmosphere, e.g. nitrogen. The duration of the reaction is about 1 to 4 hours, depending on the amount and activity of the catalyst as well as on the temperature.

After the reaction has been terminated, the residues of catalyst can readily be separated from the reaction product by decanting, filtration, or centrifuging.

If starting materials of sufficient purity are utilized, the ethylbenzene prepared according to the method of the present invention is so pure that additional purification operations (e.g. distillation) are no longer required, and the ethylbenzene thus produced can be dehydrogenated directly to styrene after the catalyst residues have been removed.

The advantages attainable by means of the present invention reside in that the aforementioned cycloolefins can be converted practically quantitatively into ethylbenzene at low temperatures and within short reaction periods, wherein the practically quantitatively formed reaction product, ethylbenzene, is so pure that it can be further processed without any other purification operations (for example to produce styrene).

EXAMPLES

Preparation of the Catalysts

A commercial available aluminum oxide having a specific surface area of 120 m²/g according to BET (Brunauer, Emmet & Teller method to determine specific surface area) and consisting of 98 percent by weight of $Al_2O_3$, where 95 percent is in the γ-form and 5 percent is in the α-form, is dried for 15 hours at 400° C under nitrogen in a container equipped with an agitator. The aluminum oxide is then allowed to cool to 150° C, and the stoichiometric amount of metallic sodium is added thereto. The sodium melts and is distributed on the support by 10 hours of agitation. During the agitating step, the temperature is gradually elevated to 400° C. After cooling, the catalyst is ready for use.

EXAMPLE 1

An agitator equipped vessel is charged under normal pressure under nitrogen with 150 g. of 1-vinylcyclohexene-3 at a temperature of 60° C. During the course of 0.5 hour, 10 g. of a catalyst containing 10 percent by weight of sodium and prepared according to the above directions is added in portions of respectively 1 gram each. The weight ratio of sodium to vinylcyclohexene is 1 : 150. After the addition of the catalyst, the reaction commences spontaneously with the evolution of hydrogen. After adding the last portion of the catalyst, the temperature is raised to about 125° C. The duration of the reaction is, in total, about 2.5 hours. The reaction product has the following composition:

97.4 percent by weight of ethylbenzene
1.9 percent by weight of ethylcyclohexene
0.02 percent by weight of ethylcyclohexane
0.5 percent by weight of unidentified residue.

The reaction took place practically quantitatively.

EXAMPLE 2

An agitator equipped vessel is charged under normal pressure and under a protective gas with 10 g. of the catalyst, containing 10 percent by weight of sodium, in 25 g. of ethylbenzene as the suspension agent. The suspension thus obtained, is heated to 120° C and 1-vinyl-cyclohexene-3, preheated to 120° C, is added thereto at a rate of 300 grams per hour.

After one hour, the reaction product has the following composition:
0.5 percent by weight of forerun
0.32 percent by weight of 1-vinylcyclohexene-3
1.5 percent by weight of vinylcyclohexane
94.3 percent by weight of ethylbenzene
0.5 percent by weight of intermediate product 1 (mass 108)
2.6 percent by weight of intermediate product 2 (mass 108).

The intermediate products 1 and 2 having the mass of 108 occur at the beginning of the reaction. They can be completely converted into ethylbenzene in a secondary reaction. The secondary reaction is carried out by allowing the reaction product to remain in contact with the catalyst at the reaction temperature for an additional period of 1 - 2 hours. In this way, a reaction product is obtained with an ethylbenzene content of 97.4 percent by weight.

EXAMPLE 3

(Comparative Example)

150 g. of 1-vinylcyclohexene-3 is agitated under normal pressure and under a protective gas for 16 hours with 3 g. of metallic sodium without a support at a temperature of 125° C. The weight ratio of sodium to vinylcyclohexene is 1 : 50. At the end of the time allotted for the experiment, the charged vinylcyclohexene is present in unchanged form. No reaction whatever has taken place.

EXAMPLE 4

(Comparative Example)

Example 3 is repeated with the alteration that the agitation is conducted for 12 hours in an agitator equipped autoclave at a temperature of 157° C. After the experiment is terminated, it is found that no ethylbenzene whatever has been formed, but that merely an isomerization has taken place to a minor extent (<10 percent) of the charged vinylcyclohexene, thus forming the intermediate products 1 and 2 (see Example 2).

EXAMPLE 5

Example 1 is repeated, but with a catalyst containing 5 percent by weight of sodium. The weight ratio of sodium to vinylcyclohexene is 1 : 100. The reaction product contains 60 percent by weight of ethylbenzene in addition to unreacted vinylcyclohexene.

EXAMPLE 6

Analogously to Example 1, 1-vinylcyclohexene-3 is treated at 80° C with a catalyst containing 15 percent by weight of sodium (weight ratio Na : vinylcyclohexene = 1 : 100).

The reaction product has the following composition:
1.08 percent by weight of forerun
0.04 percent by weight of 1-vinylcyclohexene-3
6.6 percent by weight of vinylcyclohexane
92.0 percent by weight of ethylbenzene
0.27 percent by weight of intermediate products 1 and 2.

EXAMPLE 7

Analogously to Example 1, 1-vinylcyclohexene-3 is treated at 120° C with a catalyst containing 20 percent by weight of sodium. The reaction product has the following composition:
0.92 percent by weight of forerun
2.1 percent by weight of 1-vinylcyclohexene-3
4.8 percent by weight of vinylcyclohexane
86.7 percent by weight of ethylbenzene
5.1 percent by weight of intermediate products 1 and 2.

EXAMPLE 8

Example 1 is repeated with a starting material having the following composition:
36 percent by weight of 1-vinylcyclohexene-3
36 percent by weight of (1-vinylcyclohexene-1, (ethylidenecyclohexenes, (ethylcyclohexadienes
28 percent by weight of ethylbenzene The reaction product has the following composition:
1.1 percent by weight of forerun
1.75 percent by weight of 1-vinylcyclohexene-3
4.5 percent by weight of vinylcyclohexane
91.4 percent by weight of ethylbenzene
1.1 percent by weight of intermediate products 1 and 2.

EXAMPLE 9

Analogously to Example 1, 1-vinylcyclohexene-3 is treated at 120° C with a catalyst containing 8 percent by weight of sodium. The reaction product has the following composition:
0.94 percent by weight of forerun
1.3 percent by weight of 1-vinylcyclohexene-3
3.7 percent by weight of vinylcyclohexane
92.3 percent by weight of ethylbenzene
1.3 percent by weight of intermediate products 1 and 2.

I claim:

1. In the method for the production of ethylbenzene by catalytic dehydrogenation of cycloolefins having 8 carbon atoms and 2 double bonds in the presence of aromatization catalysts, the improvement comprising: said cycloolefins having a 6 carbon atom ring with at least one double bond, said dehydrogenation is carried out at a temperature of about 20° to 150° C and under a pressure of about 0.8 to 2 atmospheres, and said aromatization catalysts consisting essentially of about 5 to 25 percent by weight of an alkali metal and about 75 to 95 percent by weight aluminum oxide support.

2. The method of claim 1, wherein said temperature is about 40° to 130° C.

3. The method of claim 2, wherein said pressure is atmospheric.

4. The method of claim 3, wherein said catalysts contain about 8 to 15 percent of said alkali metal.

5. The method of claim 3, wherein said catalysts contain about 10 percent of said alkali metal.

6. The method of claim 3, having a weight ratio of alkali metal to cycloolefins of about 1 : 1000 to 1 : 30.

7. The method of claim 6, wherein said weight ratio is about 1 : 150 to 1 : 50.

8. The method of claim 7, wherein said alkali metal is sodium.

9. The method of claim 8, wherein said aluminum oxide is γ-aluminum oxide.

10. The method of claim 1, wherein said cycloolefins are selected from the group consisting of cis -(1) - ethylidene -cyclohexene (2), trans -(1) -ethylidenecyclohexene -(2), 1-ethyl -cyclohexadiene -(1,3), 2-ethyl -cyclohexadiene-(1,3), 1-ethyl-cyclohexadiene -(1,4) and 1-vinylcyclohexene-3.

* * * * *